United States Patent [19]

Le Foyer de Costil et al.

[11] Patent Number: 4,545,990

[45] Date of Patent: Oct. 8, 1985

[54] ANTI-ACNE COMPOSITION

[75] Inventors: Carol Le Foyer de Costil; Liliane Ayache, both of Paris; Jean-Paul Tisseyre, Saint-Cloud, all of France

[73] Assignee: L'Oreal, Paris, France

[21] Appl. No.: 553,977

[22] Filed: Nov. 21, 1983
(Under 37 CFR 1.47)

[30] Foreign Application Priority Data

Nov. 22, 1982 [LU] Luxembourg .............................. 84485

[51] Int. Cl.[4] ..................... A61K 31/70; A61K 35/78; A61K 31/235
[52] U.S. Cl. ...................................... 514/557; 514/21; 514/729; 514/568; 514/714; 424/195.1
[58] Field of Search ............... 424/195, 338, 180, 343, 424/62, 359, 308; 514/240

[56] References Cited

U.S. PATENT DOCUMENTS

| 3,535,422 | 10/1970 | Cox et al. | 424/338 |
| 4,056,611 | 11/1977 | Young | 424/338 |
| 4,318,907 | 3/1982 | Kligman et al. | 424/338 |
| 4,350,681 | 9/1982 | Fulton | 424/338 |
| 4,355,028 | 10/1982 | Kligman et al. | 424/338 |
| 4,428,933 | 1/1984 | King | 424/338 |

FOREIGN PATENT DOCUMENTS

| 2037M | 9/1963 | France | 424/195 |
| 48-19942 | 6/1973 | Japan | 424/195 |
| 0086199 | 7/1981 | Japan | 424/195 |

Primary Examiner—Dale R. Ore
Attorney, Agent, or Firm—Cushman, Darby & Cushman

[57] ABSTRACT

A composition for the local treatment of acne comprises from 1 to 20 weight percent of benzoyl peroxide and at least one other active principle selected from collagenic palmitoyl acid, glycyrrhetinic acid, bisabolol and a meristem extract.

10 Claims, No Drawings

ANTI-ACNE COMPOSITION

The present invention relates to a new anti-acne composition, based on benzoyl peroxide, in combination with at least one other active principle so as to obtain a synergistic, as well as complementary, effect in the treatment of acne.

Acne is generally experienced by young people, in the 14 to 30 years old age group and has for its essential origin a hormonal disorder which manifests itself by the appearance of pimples, blackheads or pustules on the face, the neck and at times the back and chest, the sebaceous glands being under the direct control of the androgenous hormonal system.

This manifestation of acne is caused essentially by hyperkeratinization of the sebaceous gland ducts which contracts the passages to that the sebum cannot flow freely and forms thus a favorable environment for bacteria proliferation.

Various therapeutic agents are known for the treatment of acne so as to prevent obstruction of the follicular duct or to counteract bacteria infections which cause inflammation phenomena.

Therapeutic agents which prevent obstruction of the follicular ducts are known under the name of keratolytic agents and include such materials as sulfur, resorcinol, salicylic acid and benzoyl peroxide.

In the treatment of acne, benzoyl peroxide is considered a strong keratolytic agent agent, possessing not only antibacterial properties but also certain secondary effects so that its use cannot be prescribed for certain people.

In effect, benzoyl peroxide is particularly irritating and causes itching even when it is applied to the acne lesions in relatively weak concentrations.

In order to avoid these irritating phenomena, it has already been proposed to combine benzoyl peroxide with certain agents such as, for example, salicylic acid or guanidine derivatives. However, these known compositions do not provide totally satisfactory results, vis-a-vis the sensitivity of the skin to benzoyl peroxide.

The present invention provides a new anti-acne composition containing, as the keratolytic agent, benzoyl peroxide together with another active principle capable of imparting a synergistic, as well as a complementary, effect in the treatment of acne.

Various tests which have been carried out have shown, in effect, that the compositions of the present invention while being stable over prolonged periods of time, also are effectively employed without encountering known secondary effects of benzoyl peroxide.

The present invention thus relates to a new benzoyl peroxide based composition for the local treatment of acne containing 1 to 20 percent by weight of benzoyl peroxide and at least one other active principle selected from the group consisting of collagenic palmitoyl acid, glycyrrhetinic acid, bisabolol and an meristem extract.

These different active principles favorably suppress or eliminate the irritating action of benzoyl peroxide on the skin so that the compositions, according to the invention, can be applied to the skin without any particular precautionary measures being required and without it being necessary that the treatment be carried out under medical supervision.

In accordance with the composition of the present invention, benzoyl peroxide preferably is present therein in an amount between 2.5 and 10 weight percent and the other active principle, as defined above, is present in an amount between 0.1 and 15 weight percent. The benzoyl peroxide is preferably employed in the form of a finely divided powder in the dry or moist state and preferably is used in a moist or wet form.

Collagenic palmitoyl acid is a substance obtained by combining palmitic acid with collagen fractions from animal skin and, more particularly, by the action of palmitoyl chloride on collagen, which has previously been chemically or enzymatically hydrolyzed.

Collagenic palmitoyl acid which is provided in the form of a waxy solid insoluble in water and partially soluble in conventional solvents, has a melting point between 65° and 75° C. depending upon the proportion of peptides linked to carbonyl group proceeding from the carboxyl group of the fatty acid.

The collagenic palmitoyl acid used in accordance with the invention is more particularly described in French Pat. No. 1,431,698.

The concentration of collagenic palmitoyl acid in the anti-acne composition of the present invention is preferably between 2 and 15 weight percent based on the total weight of the composition.

Glycyrrhetinic acid (or glycyrrhetic acid) is a natural acid extract of licorice roots having the gross formula, $C_{30}H_{46}O_4$ (molecular weight 470). This material can be provided in the 18α form (melting point 335° C.) or 18β form (melting point 296° C.).

According to the present invention glycyrrhetinic acid is preferably employed at a concentration between 0.1 and 3 weight percent relative to the total weight of the composition.

Bisabolol is a tertiary, non-saturated monocyclic sesquiterpenic alcohol of the formula:

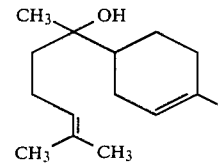

whose gross formula is $C_{15}H_{26}O$ (molecular weight 222).

It is a viscous, colorless, slightly yellowish liquid whose essential oil of camomille can contain up to 50 percent of the form (−)-α-bisabolol.

The anti-acne composition according to the present invention contains, preferably, from 0.5 to 5 weight percent bisabolol relative to the total weight of the composition.

The meristem extract is a water soluble extract derived from the root tips of leaf-bearing trees (angiospermes) and is provided in the form of a deep brown liquid having a slight, but characteristic, odor.

The meristem extract is essentially characterized by the presence of 3,4,5-trihydroxybenzoic acid or gallic acid.

In accordance with the present invention, the anti-acne composition contains from 1 to 10 weight percent of the meristem extract in the form of a 0.4 weight percent aqueous solution of the pure extract, this solution having a pH between 6 to 7 and a refractive index, $(n_D^{20})$, between 1.310 and 1.360.

The anti-acne composition in accordance with the present invention can be provided under various forms, principally under the form of an ointment, an emulsion or a gel.

The term "ointment" includes such formulations as creams containing absorbable oleaginous bases, for example, petrolatum, lanolin, polyethylene glycols as well as mixtures thereof.

These ointments can be prepared by the dispersion of the benzoyl peroxide and the other active compound with which it is combined in a conventional base, such as petrolatum, lanolin, polyethylene glycols and mixtures thereof. The benzoyl peroxide and the active compound are finely divided by means of a colloidal mill, using for example slightly liquid petrolatum as the levigating agent before dispersion in the ointment base.

Emulsions, be they an oil-in-water or water-in-oil type, are prepared by dispersing the benzoyl peroxide in the aqueous phase, and the said active compound with which benzoyl peroxide is associated, is dispersed, depending upon its affinity characteristics, either in the oily phase or in the aqueous phase before emulsifying the two phases.

The weight ratio of the oily phase to the aqueous phase is generally between 95:5 and 25:75.

Representative oils capable of constituting the oil phase include, for instance, animal oils such as lanolin and perhydrosqualene; vegetable oils such as sweet almond oil, avocado oil, ricin oil, olive oil, grape seed oil, poppy seed oil, colaz oil, peanut oil, corn oil, hazelnut oil, jojoba oil, safflower oil, wheat germ oil, karite butter and the fat of Shorea robusta; mineral oils such as, for example, paraffin oil; and silicone oils soluble in other oils.

Also certain synthetic products such as, for example, saturated esters and principally isopropyl palmitate, isopropyl myristate, butyl myristate, cetyl myristate, hexadecyl stearate, ethyl palmitate as well as triglycerides of octanoic and decanoic acids, cetyl ricinoleate, purcellin oil and hydrogenated polyisobutene can be used.

The oil phase of the emulsions can also contain certain waxes and principally carnauba wax, bees wax, ozokerite and candellila water.

These compositions in the form of emulsions can also contain other components such as preservatives, pigments, humectants and charges such as talc and powders of nylon, starch and polyethylene.

Gels made in accordance with the present invention are semi-solid formulations prepared by gelling a suspension of benzoyl peroxide and the active compound associated therewith using such gelling agents as "bentone gel", sold by NL Industries, for an oily phase, or crosslinked polyacrylic acid, for an aqueous phase, a representative crosslinked polyacrylic acid being one sold by Goodrich under the tradename Carbopol 940 or 941 and being used in neutralized form.

If desired a nonionic surfactant can be introduced into the gel so as to provide better dispersion and availability of the benzoyl peroxide. A lower aliphatic alcohol such as ethanol can be incorporated in the gel in an amount of 5 to 40 weight percent, as can, optionally, a silicone oil and glycols, such as polypropylene glycol or polyethylene glycol.

In the treatment of acne, the composition of the present invention, as defined above, is applied at least once each day on the acne lesions at a rate of 0.5 to 10 mg/cm$^2$, the duration of the treatment being of the order of 2 to 4 weeks according to the area of the skin affected.

The following non-limited examples are given to illustrate the invention.

EXAMPLE 1

An anti-acne gel in accordance with the present invention is prepared by admixing the following components:

| | |
|---|---|
| Carbopol 940 (polyacrylic acid sold by Goodrich) | 1 g |
| Triethanolamine, sufficient amount for pH 5 | 0.3 g |
| Propylene glycol | 12 g |
| Glycerine | 5 g |
| Preservative | 0.3 g |
| Benzoyl peroxide | 10 g |
| Bisabolol | 2 g |
| Water, sufficient for | 100 g |

In this example, the bisabolol can be replaced by 2 g of glycyrrhetinic acid with equally favorable results.

EXAMPLE 2

An anti-acne cream in the form of an oil-in-water emulsion is prepared by admixing the following components:

| | |
|---|---|
| Polyethylene glycol stearate oxyethylenated with 20 moles of ethylene oxide | 3.85 g |
| Mixture of glycerol mono- and di-stearate | 0.7 g |
| Cetyl alcohol | 2.45 g |
| Petrolatum oil | 10 g |
| Mixture of 90% stearyl alcohol and 10% sodium lauryl sulfate sold under the trade name "Sinnowax SX" by Henkel | 4 g |
| Silicone oil | 0.2 g |
| Preservative | 0.3 g |
| Xanthane gum | 1 g |
| Benzoyl peroxide | 8 g |
| Collagenic palmitoyl acid | 8 g |
| Water, sufficient amount for | 100 g |

EXAMPLE 3

An anti-acne cream in accordance with the present invention is prepared by admixing the following components:

| | |
|---|---|
| Polyethylene glycol stearate oxyethylenated with 20 moles of ethylene oxide | 6 g |
| Mixture of glycerol mono- and di-stearate | 1.1 g |
| Cetyl alcohol | 3.5 g |
| Sweet almond oil | 8 g |
| Isopropyl myristate | 8 g |
| "Sinnowax SX" (as in Ex. 2) | 4 g |
| Carbopol 941 (neutralized with triethanolamine) | 0.2 g |
| Benzoyl peroxide | 10 g |
| Aqueous meristem extract (0.4% aqueous solution of pure extract, sold under the trade name "Meristem-Extract" by Grau Aromatics) | 10 g |
| Preservative | 0.3 g |
| Water, sufficient amount for | 100 g |

EXAMPLE 4

An anti-acne gel in accordance with the present invention is prepared by admixing the following components:

| | |
|---|---:|
| Veegum HV | 0.9 g |
| Xanthane gum | 0.4 g |
| Propylene glycol | 10 g |
| Glycerine | 6 g |
| Preservative | 0.3 g |
| Benzoyl peroxide | 12 g |
| Bisabolol | 1.5 g |
| Water, sufficient amount for | 100 g |

EXAMPLE 5

An anti-acne gel in accordance with the present invention is prepared admixing the following components:

| | |
|---|---:|
| Xanthane gum | 1.5 g |
| Propylene glycol | 12 g |
| Glycerine | 3 g |
| Tween 20 (polyoxyethylenated sorbitan monooleate) | 2 g |
| Preservative | 0.3 g |
| Benzoyl peroxide | 8 g |
| Glucyrrhetinic acid | 2 g |
| Water, sufficient amount for | 100 g |

With daily application of the compositions of Examples 1–5, above, on acne lesions on the face and neck and by continuing this regimen for about 3 weeks a very clear improvement is achieved and most of the lesions disappear. The compositions are, moreover, very well received by patients, especially since they do not cause any itching.

What is claimed is:

1. An anti-acne composition for local treatment of acne comprising benzoyl peroxide in an amount of 1 to 20 weight percent based on the total weight of said composition and at least one other active principle present in an amount of 0.1 to 15 weight percent based on the total weight of the composition so as to suppress or eliminate the skin irritating action of benzoyl peroxide and being selected from the group consisting of collagenic palmitoyl acid, glycyrrhetinic acid, bisabolol having the formula

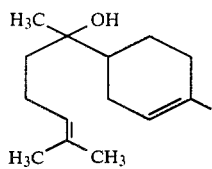

and a meristem extract which is a water soluble extract derived from the root tip of leaf-bearing trees and comprising 3,4,5-trihydroxybenzoic acid or gallic acid in an ointment, emulsion or gel.

2. The composition of claim 1 wherein said benzoyl peroxide is present in an amount of 2.5 to 10 weight percent based on the total weight of said composition.

3. An anti-acne composition for local treatment of acne comprising an ointment, emulsion, or gel containing benzoyl peroxide present in an amount of 1 to 20 weight percent based on the total weight of said composition and collagenic palmitoyl acid present in an amount of 0.1 to 15 percent by weight based on the total weight of said composition so as to suppress or eliminate the skin irritating action of benzoyl peroxide.

4. An anti-acne composition for local treatment of acne comprising an ointment, emulsion, or gel containing benzoyl peroxide present in an amount of 1 to 20 weight percent based on the total weight of said composition and glycyrrhetinic acid present in an amount of 0.1 to 15 percent by weight based on the total weight of said composition so as to suppress or eliminate the skin irritating action of benzoyl peroxide.

5. An anti-acne composition for local treatment of acne comprising an ointment, emulsion, or gel containing benzoyl peroxide present in an amount of 1 to 20 weight percent based on the total weight of said composition and bisabolol having the formula

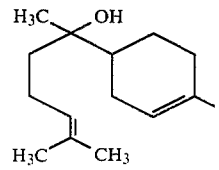

present in an amount of 0.1 to 15 weight percent based on the total weight of said composition so as to suppress or eliminate the skin irritating action of benzoyl peroxide.

6. An anti-acne composition for local treatment of acne comprising an ointment, emulsion, or gel containing benzoyl peroxide present in an amount of 1 to 20 weight percent based on the total weight of said composition and a meristem extract which is a water soluble extract derived from the root tip of leaf-bearing trees and comprising 3,4,5-trihydroxybenzoic acid or gallic acid present in an amount of 1 to 10 weight percent based on the total weight of said composition, so as to suppress or eliminate the skin irritating action of benzoyl peroxide.

7. The composition of claim 1 wherein said collagenic palmitoyl acid is present in an amount of 2 to 15 percent by weight based on the total weight of said composition.

8. The composition of claim 1 wherein said glycyrrhetinic acid is present in an amount from 0.1 to 3 percent by weight based on the total weight of said composition.

9. The composition of claim 1 wherein said bisabolol is present in an amount from 0.5 to 5 weight percent based on the total weight of said composition.

10. The composition of claim 1 wherein said meristem extract is in the form of a 0.4% aqueous solution and is present in an amount from 1 to 10 weight percent based on the total weight of said composition.

* * * * *